United States Patent
Hipp et al.

(10) Patent No.: US 8,118,729 B2
(45) Date of Patent: Feb. 21, 2012

(54) ENDOSCOPIC INSTRUMENT HAVING A ROTATABLY MOUNTED AND DETACHABLE COUPLING PART

(75) Inventors: Klaus-Peter Hipp, Bretten (DE); Ludwig Bonnet, Knittlingen (DE); Michael Fritz, Karlsruhe (DE); Thomas Ernst, Kürnbach (DE); Hubertus Riedmiller, Würzburg (DE)

(73) Assignee: Richard Wolf GmbH, Knittlingen (DE)

( * ) Notice: Subject to any disclaimer, the term of this patent is extended or adjusted under 35 U.S.C. 154(b) by 1803 days.

(21) Appl. No.: 11/231,172

(22) Filed: Sep. 20, 2005

(65) Prior Publication Data

US 2006/0063975 A1    Mar. 23, 2006

(30) Foreign Application Priority Data

Sep. 21, 2004 (DE) .................. 20 2004 014 828 U

(51) Int. Cl.
  *A61B 1/12* (2006.01)
(52) U.S. Cl. ......... 600/105; 600/156; 600/158; 600/159
(58) Field of Classification Search .................. 600/105, 600/156, 158, 159, 101; 606/46; 604/30–45, 604/533–539
See application file for complete search history.

(56) References Cited

U.S. PATENT DOCUMENTS

| | | | | |
|---|---|---|---|---|
| 3,791,379 A | * | 2/1974 | Storz | 600/158 |
| 5,151,101 A | | 9/1992 | Grossi et al. | |
| 5,287,845 A | * | 2/1994 | Faul et al. | 600/135 |
| 5,486,155 A | * | 1/1996 | Muller et al. | 600/137 |
| 6,022,334 A | | 2/2000 | Edwards et al. | |
| 6,358,200 B1 | * | 3/2002 | Grossi | 600/156 |
| 2004/0082915 A1 | * | 4/2004 | Kadan | 604/164.04 |

FOREIGN PATENT DOCUMENTS

| | | |
|---|---|---|
| DE | 41 01 472 A1 | 7/1992 |
| DE | 198 26 311 A1 | 12/1999 |
| DE | 200 04 329 U1 | 7/2000 |
| DE | 101 38 331 A1 | 2/2003 |
| DE | 20 2004 014 828 U1 | 1/2005 |

* cited by examiner

*Primary Examiner* — Matthew J Kasztejna
*Assistant Examiner* — Ryan Henderson
(74) *Attorney, Agent, or Firm* — Panitch Schwarze Belisario & Nadel LLP

(57) ABSTRACT

An endoscopic instrument with a hollow shank which on the proximal side is provided with a connection part with at least one suction connection and/or rinsing connection, with a coupling part for fixing a working insert. The coupling part is mounted rotatably with respect to the connection part and the coupling part is detachably connected to the connection part. The endoscopic instrument further includes an annular axial seal which is arranged between the connection part and the coupling part.

9 Claims, 2 Drawing Sheets

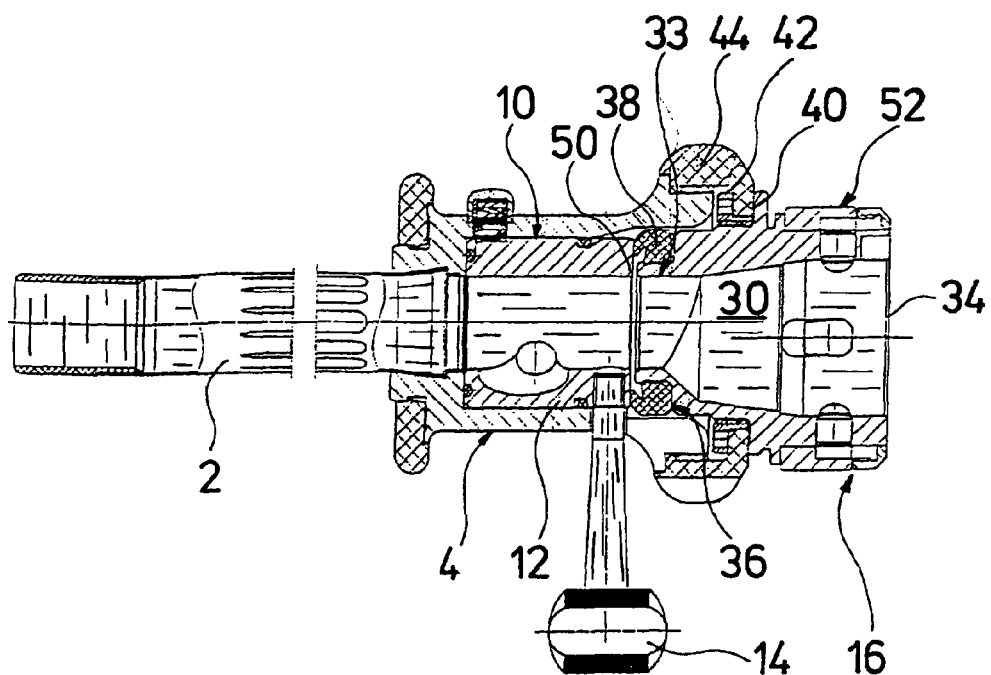
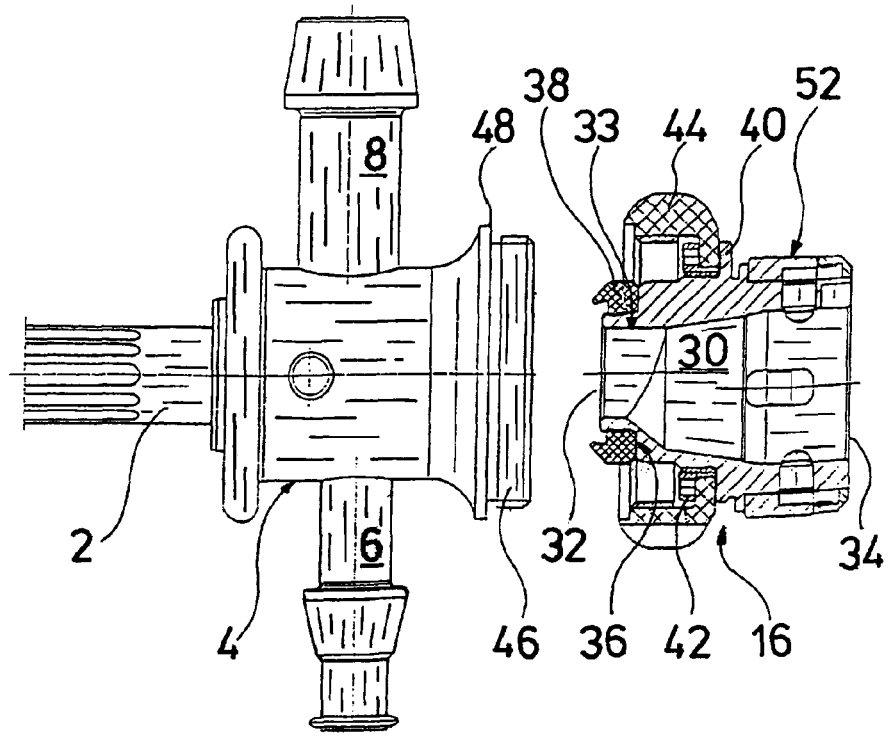

ENDOSCOPIC INSTRUMENT HAVING A ROTATABLY MOUNTED AND DETACHABLE COUPLING PART

BACKGROUND OF THE INVENTION

The invention relates to endoscopic instruments having a rotatably mounted and detachable coupling part.

Endoscopic instruments as are for example applied in resectoscopy, generally comprise a shank through which operating instruments typically in the form of a working insert are led, and these are connected to the shank at the proximal side. With these instruments and via suitable connections, a rinsing liquid is introduced into the shank, led to the region of operation and subsequently suctioned away again together with the tissue remains.

Generally, with such endoscopic instruments one differentiates between those with a continuous rinsing from those instruments with an intermittent rinsing.

The shanks of the instruments with a continuous rinsing are designed with double walls and are termed "continuous flow" shanks. With these shanks, rinsing fluid is continuously supplied to the operation region via an inner shank tube, whilst rinsing fluid is simultaneously suctioned away again via an annular gap formed by the inner and outer shank tube. It is known to design endoscopic instruments with a "continuous flow" shank such that a working insert led in the inner shank tube may be rotated together with the inner shank tube, whilst the outer shank tube is not rotated. This is advantageous, since a rotation of the outer shank could traumatize the tissue which surrounds it. However in contrast, there exits the disadvantage that the outer diameter of "continuous flow" shanks is very large which is intrinsic of their design, and that the body tissue which surrounds the shank is burdened in a different manner.

Endoscopic instruments with an intermittent rinsing with which an equally large sling is applied for removing tissue as with the continuous flow shanks do not have this disadvantage. Such instruments have a simple hollow shank, so that the outer diameter may be designed significantly smaller than with "continuous flow" shanks. However the disadvantage with these shanks is again that the working insert may only be rotated together with the shank.

Known endoscopic instruments with an intermittent rinsing attempt to avoid this disadvantage, in which the working insert in combination with the hollow shank may be rotated and the conduit connections with the flexible tubings connected thereto remain stationary on rotation of the working insert. However by way of this, a traumatization of the tissue, for example a urethra is not reduced as is desired.

BRIEF SUMMARY OF THE INVENTION

Against this background, it is an object of the present invention to create an endoscopic instrument which avoids the above-mentioned disadvantages and which is simple to clean.

The endoscopic instrument according to the invention is typically designed such that it rinses in an intermittent manner. It comprises a hollow shank which on the proximal side is provided with a connection part with at least one suction and/or rinsing connection as well as a coupling part for fixing a working insert, wherein the coupling part is rotatably mounted with respect to the connection part. The instrument furthermore comprises means for the detachable connection of the coupling part and connection part, and an annular axial seal which is arranged between the connection part and the coupling part.

On the proximal side, a coupling part is arranged on the connection part. The coupling part serves for fixing the working insert which is led through the shank tube. According to the invention, the coupling part is connected to the connection part in a detachable manner such that the coupling part is rotatable with respect to the connection part. This permits a rotation of the working insert during the endoscopic operation without the hollow shank of the endoscopic instrument being co-rotated. In this manner, a burdening of the patient may be prevented, for example a traumatization of the body tissue surrounding the shank which may occur on rotation of the shank. The connection part with the endoscopic instrument according to the invention is not co-rotated on rotation of the working insert, so that an operator e.g. is not inhibited by way of a flexible tubing or flexible tubings which rotate and are connected to the connection on the connection part. The detachable connection of the coupling part and the connection part further permits the coupling part to be separated quickly and simply from the connection part for cleaning purposes for example, and for these to be joined together again at a later stage.

The coupling part is sealed with respect to the connection part via an annular axial seal. The axial seal is arranged such that it bears on the coupling part and the connection part in a sealing manner. Apart from the axial seal, with the endoscopic instrument according to the invention no further seals are required in order to seal the connection part with respect to the coupling part. The axial seal preferably lies on an end-face of the connection part at the proximal side and on an end-face of the coupling part at the distal side. With this, the axial seal may be connected to the connection part at the proximal side and may seal this with respect to a rotating distal end-face of the coupling part.

The axial seal is preferably arranged on the coupling part at the distal side and co-rotates with the coupling part whilst it sealingly bears on an end-face of the connection part. On account of the rotation of the axial seal relative to the stationary connection part, the axial seal is preferably to be formed of a material which apart from having good sealing properties also has a low coefficient of friction. The axial seal is preferably formed of an elastomeric plastic, but other materials which have the above-mentioned material properties are also conceivable.

At the distal side, the coupling part preferably has a hollow-cylindrical section which is designed in a stepped manner. The axial seal is advantageously supported on one end-face of the stepped part of the hollow-cylindrical section. The end-face is annular and is formed by a stepping of the outer contour of the coupling part, said stepping being arranged at the distal end of the hollow-cylindrical section. The axial seal rests on this end-face such that it is fixed on the coupling part in the radial as well as axial direction. The end-face is advantageously distanced so far from the distal end of the coupling part that an axial seal bearing on this end-face projects beyond the step and thus the coupling part in the axial direction. In this manner the axial seal, when the coupling part is connected to the connection part, may be sealingly clamped in between the end-face of the hollow-cylindrical section and an end-face on the connection part, and the coupling part may be sealed with respect to the connection part. Furthermore, this arrangement has the advantage that the axial seal may be exchanged in a simple manner after releasing the coupling part or may be removed and assembled for cleaning purposes.

In one advantageous embodiment of the endoscopic instrument according to the invention, the connection part comprises a slide valve. This selectively connects the hollow shank to a rinsing channel or suction channel. In this case two connections are arranged on the connection part. With this, the proximal end-side of the rotary slide of the slide valve is simultaneously used as a bearing surface and sealing surface for the axial seal. The rotary slide of the slide valve is arranged in the connection part in a fluid-tight manner such that in each case it only releases one of these connections, i.e. that it either connects only the rinsing channel or the suction channel, which in each case are connected to one of these connections, to the hollow shank. The operator by way of actuating the slide valve may connect the hollow shank to the rinsing connection or to the suction connection. Furthermore it is possible to set the rotary slide into a neutral position in which both connections are closed by the rotary slide. Preferably the rotary slide of the slide valve is arranged at the proximal end of the connection part such that it may be easily removed from the connection part for cleaning. A proximal end-face of the rotary slide may then form the bearing surface for the axial surface arranged on the coupling part, and the axial seal is supported on this axial surface at the distal side.

The coupling part is advantageously mounted in a rotatable manner with respect to the means for the detachable connection of the coupling part on the connection part. The connection means themselves are then connected to the connection part in a rotationally fixed manner.

Preferably the means for the detachable connection of the coupling part and the connection part comprise a union nut arranged on the coupling part and an outer thread arranged on the connection part. The union nut and the outer thread arranged on the connection part are then usefully screwable against an abutment in a manner such that the coupling part is always freely rotatable with respect to the connection part.

The abutment may be arranged on the union nut as well as on the connection part, but is preferably formed on the connection part. If the union nut is screwed on the connection part, the abutment limits the common thread flight of the union nut and the outer thread in this manner.

The union nut is held with a positive fit between an end-face on the outer periphery of the coupling part and a fixation ring which is arranged on a peripheral surface of the hollow-cylindrical lug of the coupling part. The union nut which engages over the outer periphery of the coupling part in the region of the hollow-cylindrical attachment with a small play is connected to the coupling part in a manner such that the coupling part is rotatable with respect to the union nut, but is held on this with a positive fit. Since the union nut needs to be rotatable in any case, it is particularly favorable to also provide the rotatable mounting between the coupling part and the connection part here.

The end-face on the outer periphery of the coupling part may advantageously be formed by a shoulder on the outer side of the coupling part, said shoulder providing the union nut on the coupling part with a proximal-side rest surface and thus may form the axial bearing for accommodating forces in the proximal direction. The fixation ring at the distal-side end-face of the union nut is rotatably mounted on the coupling part on the peripheral surface of the hollow-cylindrical lug with little axial play.

For fastening the fixation ring on the peripheral surface of the hollow-cylindrical projection, the fixation ring advantageously comprises an inner thread with which it meshes into an outer thread which is provided on a peripheral surface of the hollow-cylindrical projection. This permits a simple attachment of the union nut on the coupling part. The fixation ring at the same time forms an abutment which fixes the bearing play with which the union nut is rotatably mounted on the coupling part.

In one advantageous embodiment of the invention the hollow shank of the endoscopic instrument and the distal-side opening of the coupling part which faces the hollow shank are aligned, wherein the proximal-side opening of the coupling part is arranged eccentrically to the opening at the distal side. This embodiment is preferably provided for the application of those working inserts which with respect to the common longitudinal axis are not rotationally symmetrical over the whole length. These working inserts for example have a section on which they are fixed to the coupling part and which is aligned eccentrically to the section of the working insert which is guided in the hollow shank. Furthermore, such working inserts may have different diameters in these sections. The coupling part is designed according to the shape of these working inserts, so that with regard to the endoscopic instrument, only the working inserts provided for this instrument may be applied. In order despite the eccentricity of the working inserts to be able to rotate these with the coupling part with respect to the connection part or with respect to the hollow shank, it is envisaged for the hollow shank and the distal-side opening of the coupling part which faces the hollow shank to be aligned, i.e. have a common middle axis.

At this location it is to be pointed out that the coupling part according to the invention may not only be used with endoscopic instruments with a simple hollow shank, but also with those instruments which are continuously rinsed and accordingly have a double-walled "continuous flow" shank, so that these instruments may also profit from the low cleaning and maintenance expense which the coupling part requires.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 2 is an enlarged representation, the connection part with the coupling part of the instrument which is attached thereto, according to FIG. 1, and FIG. 3 is a lateral view of the connection part according to FIG. 2 with a coupling part arranged separately, in section.

DETAILED DESCRIPTION OF THE INVENTION

Figure 1:
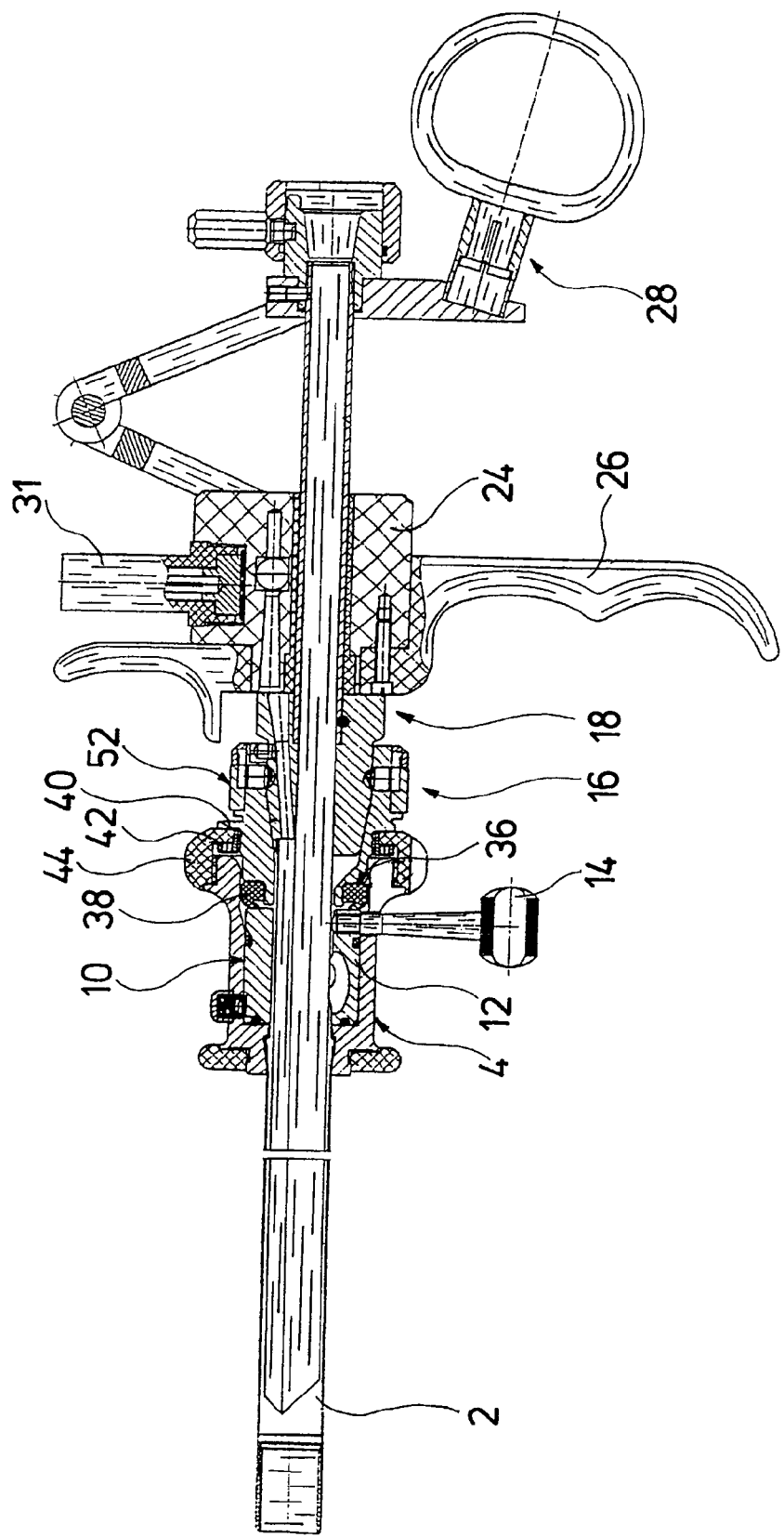
FIG. 1 is a longitudinal section of an endoscopic instrument according to the invention.

With the endoscopic instrument represented in FIG. 1, it is the case of a resectoscope with a hollow shank 2 at the distal side, on whose proximal end a connection part 4 is arranged. As is evident from FIG. 3, the connection part 4 comprises a conduit connection 6 for introducing a rinsing fluid into the hollow shank 2 as well as a conduit connection 8 for suctioning the rinsing fluid from the hollow shank 2. The conduit connection 6 or the conduit connection 8 may be selectively closed or released by way of a slide valve arranged in the connection part 4. In a middle position, the slide valve 10 closes the conduit connection 6 as well as the conduit connection 8. For this, the slide valve 10 comprises a rotary slide 12 which with the help of lever 14 may be rotated about the longitudinal axis of the hollow shank 2 such that in a first position of the rotary slide 12, the connection 6 is released and the connection 8 is closed, and in a second position, the connection 6 is closed and the connection 8 is released.

A coupling part 16 connects to the connection part 4 at the proximal side. A working insert 18 which is known per se and for this reason is not described in detail and in which optics which are not represented as well as a HF cutting sling are guided, is fixed on this coupling part 16. The proximal end of the cutting sling is fastened in a lock body 24 which also carries the electrical connection contact 31. The cutting sling may be traveled in the longitudinal direction by way of handles 26 and 28 arranged on the lock body 24.

The coupling part 16 comprises a through-opening 30 which is complementary to the contour of the working insert 18. This through-opening 30 has an opening 32 at the distal side and an opening 34 at the proximal side, wherein the opening 34 is arranged eccentrically to the opening 32, thus only the opening 32 is aligned to the shank 2.

A hollow-cylindrical lug 33 on which a shoulder 36 is provided is formed in the region of the opening 32 facing the connection part 4 and at the end-face of the essentially cylindrical coupling part 16. A sealing ring 38 is arranged on this shoulder 36 in a manner such that it sealingly bears on an end-face formed by the shoulder 36, and on the peripheral surface formed by the shoulder. The sealing ring 38 is supported by the shoulder 36 in the radial as well as axial direction in such a manner, and in this manner is connected to the coupling part 16 in a rotationally fixed manner.

On the outer periphery of the coupling part 16, a second shoulder 40 is formed in the proximal direction behind the shoulder 36. A union nut 44 is rotatably mounted between this shoulder 40 and a round nut 42 with drilled holes in one face, which forms a fixation ring. The round nut 42 with drilled holes in one face has an inner thread with which it may be screwed onto an outer thread which is arranged on a peripheral region of the coupling part 16 which connects distally of the shoulder 40. The round nut with drilled holes in one face, at the end-face comprises an abutment ring which is designed such that the union nut 44 is mounted radially as well as axially with little play when the round nut 42 with drilled holes in one face is screwed against the shoulder 40. The union nut 44 is thus rotatable with respect to the coupling part 16 and forms an axial bearing as well as radial bearing for the coupling part 16.

The coupling part 16 may be connected to the connection part 4 via the union nut 44. For this, the connection part 4 at its proximal end on the peripheral side comprises an outer thread 46 on which the union nut 44 is screwed. In order to advance the coupling part 16 to the connection part 4 only so far, that the coupling part 16 bears on the connection part 4 in a fluid-tight manner, but that the coupling part 16 at the same time remains rotatable with respect to the connection part 4 and the shank 2 arranged thereon, and annular shoulder 48 is provided on the outer periphery of the connection part 4 distally of the outer thread 46. The shoulder 48 forms an abutment against which the union nut may be screwed on the outer thread 46, so that the coupling part is freely rotatable.

When the union nut 44 is screwed on the outer thread 46, a sealing lip which is arranged over the complete periphery of that end-face of the sealing ring 38 which faces the connection part 4 contacts a proximal-side end-face 50 of the rotary slide 12. The coupling part 16 is sealed with respect to the connection part 4 in this manner.

A coupling 52 is arranged on the coupling part 16 at the proximal side, and this coupling serves for fastening the working insert 18 in the coupling part 16. The coupling 52 is formed as known couplings of this type and is therefore not described in detail. The working insert locks automatically on introduction by way of the coupling, and the locking may be lifted against spring force when the working insert is to be removed.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An endoscopic instrument comprising:
a single walled hollow shank (2) that rinses in an intermittent manner, a proximal side of the hollow shank (2) being provided with a connection part (4) having a rinsing channel (6) and a suction channel (8), the connection part (4) comprising a slide valve (10) which selectively connects the hollow shank (2) to only the suction channel (8) and to only the rinsing channel (6);
a coupling part (16) for fixing a working insert (18), wherein the coupling part (16) is rotatably mounted directly to the connection part (4) permitting rotation of the working insert (18) during an endoscopic operation without the hollow shank (2) being co-rotated;
means (44, 46) for detachable connection of the coupling part (16) and connection part (4); and
an annular axial seal (38) provided directly between the coupling part (16) and the connection part (4), wherein the annular axial seal (38) sealingly bears on an end-face (50) of a rotary slide (12) of the slide valve (10).

2. The endoscopic instrument according to claim 1, wherein the annular axial seal (38) is arranged on the coupling part (16) at the distal side and co-rotates with the coupling part (16).

3. The endoscopic instrument according to claim 1, wherein the coupling part (16) at the distal side comprises a hollow-cylindrical section (33) which is designed in a stepped manner and which carries the axial seal (38).

4. The endoscopic instrument according to claim 1, wherein the annular axial seal (38) is supported by an end-face (36) of a stepped part of the hollow-cylindrical section (33).

5. The endoscopic instrument according to claim 1, wherein the coupling part (16) is rotatably mounted with respect to the means (44, 46) for the detachable connection of the coupling part (16) on the connection part (4).

6. The endoscopic instrument according to claim 1, wherein the means (44, 46) for the detachable connection of the coupling part (16) and the connection part (4) comprise a union nut (44) arranged on the coupling part (16), and an outer thread (46) arranged on the connection part (4), which may be screwed against an abutment (48) in a manner such that the coupling part (16) is always freely rotatable with respect to the connection part (4).

7. The endoscopic instrument according to claim 1, wherein a union nut (44) is held with a positive fit between a peripheral-side end-face of the coupling part (16) and a fixation ring (42) arranged on a peripheral surface of the hollow-cylindrical lug (33) of the coupling part (16).

8. The endoscopic instrument according to claim 7, wherein the fixation ring (42) comprises an inner thread and is screwed on an outer thread which is arranged on a peripheral surface of the hollow-cylindrical lug (33) of the coupling part (16).

9. The endoscopic instrument according to claim 1, wherein the hollow shank (2) and a distal-side opening (32) of the coupling part (16) which faces the hollow shank (2) are aligned, and a second opening (34) of the coupling part (16) which is arranged at the proximal side, is arranged eccentrically to the distal-side opening (32).

* * * * *